United States Patent [19]

Komai et al.

[11] 4,093,786
[45] June 6, 1978

[54] 1,1-BIS(TERT-BUTYLPEROXY)CYCLODO-DECANE

[75] Inventors: Takeshi Komai; Masaru Matsushima; Takeshi Nakajima, all of Aichi, Japan

[73] Assignee: Nihon Yushi Co., Ltd., Tokyo, Japan

[21] Appl. No.: 623,401

[22] Filed: Oct. 17, 1975

[30] Foreign Application Priority Data

Oct. 22, 1974 Japan .............................. 49-120959

[51] Int. Cl.$^2$ ............................................. C08F 8/06
[52] U.S. Cl. ..................... 526/57; 260/42.29; 260/42.32; 260/42.33; 260/42.37; 260/610 R; 260/879; 526/29; 526/41; 526/47
[58] Field of Search ............. 260/610 R, 42.29, 42.32, 260/42.33, 42.37; 526/57, 29, 41, 47

[56] References Cited

U.S. PATENT DOCUMENTS

| | | | |
|---|---|---|---|
| 2,750,421 | 6/1956 | Halbig | 260/610 R |
| 3,296,184 | 1/1967 | Portolani et al. | 260/610 R X |
| 3,342,872 | 9/1967 | Gerritsen et al. | 260/610 R |
| 3,357,964 | 12/1967 | Gulpen et al. | 260/610 R X |
| 3,468,962 | 9/1969 | Ballini et al. | 260/610 R |

FOREIGN PATENT DOCUMENTS

38-24372 11/1963 Japan .............................. 260/610 R

*Primary Examiner*—William F. Hamrock
*Attorney, Agent, or Firm*—Blanchard, Flynn, Thiel, Boutell & Tanis

[57] ABSTRACT

1,1-bis(tert-butylperoxy)cyclododecane derived from cyclododecanone and tert-butylhydroperoxide has the formula

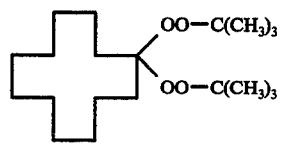

and is a new, stable and solid compound particularly suitable as a crosslinking agent of polymeric materials.

9 Claims, 1 Drawing Figure

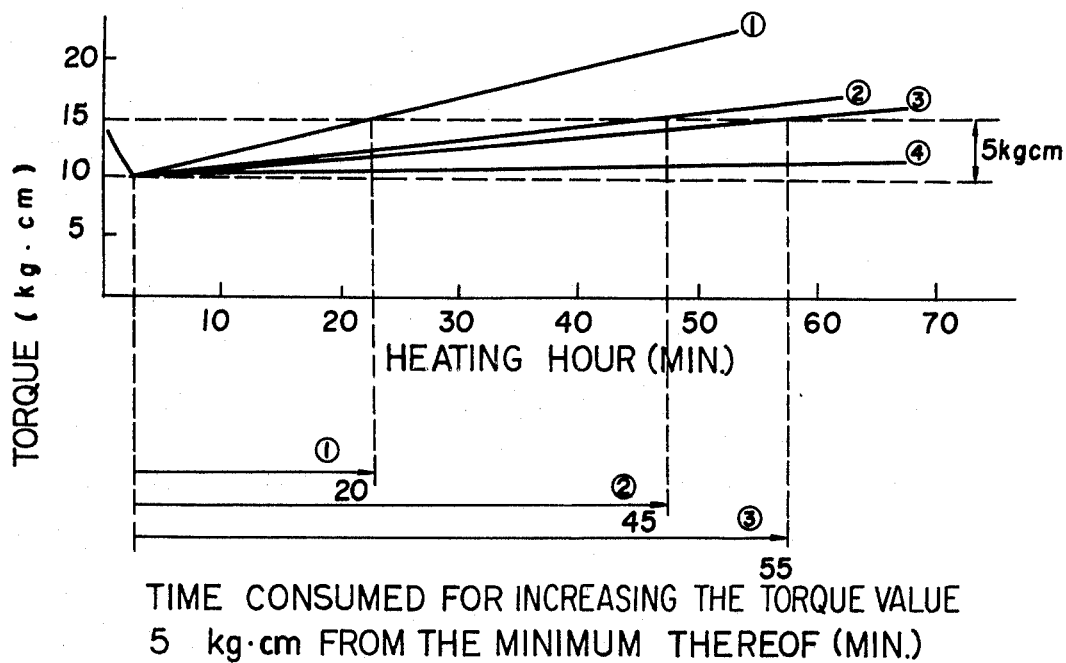

1,1-BIS(TERT-BUTYLPEROXY)CYCLODODECANE

BACKGROUND OF THE INVENTION

1. Field of the Invention

The present invention relates to 1,1-bis(tert-butylperoxy)cyclododecane, a novel solid and stable compound, and its use as a crosslinking or curing agent.

2. Description of the Prior Art

It has been disclosed that bisperoxyketals can be used, together with dialkylperoxides, e.g., dicumyl peroxide, for crosslinking or curing natural rubber, synthetic rubber and ethylene homo-polymers and copolymers. Bisperoxyketals can lower the crosslinking temperature, since the thermal decomposition temperature of bisperoxyketals is lower than that of dialkyl peroxides.

U.S. Pat. No. 2,455,569 discloses an extensive use of bisperoxyketals and bisperoxyacetals. However, it does not make reference to their use as crosslinking catalysts.

German Pat. No. 945,187 discloses the use of 2,2-bis(tert-butylperoxy)butane and 1,1-bis(tert-butylperoxy)-3,3,5-trimethylcyclohexane as catalysts for a rubber vulcanizing process.

U.S. Pat. No. 3,296,184 discloses the combined use of 2,2-bis(tert-butylperoxy)butane, 1,1,7,7-tetra(tert-(butylperoxy)cyclododecane and sulfur for crosslinking olefin homo-polymers and copolymers.

British Pat. No. 1,044,010 discloses the use of 2,2-bis(4,4-di-tert-butylperoxy cyclohexyl)propane as a catalyst for crosslinking. This compound has about the same thermal decomposition rate as that of 1,1-bis(tert-butylperoxy)-3,3,5-trimethylcyclohexane.

U.S. Pat. No. 3,433,825 discloses esters of 4,4-bis(tert-butylperoxy)pentanoic acid. These peroxides have a thermal decomposition rate slower than that of 1,1-bis(tert-butylperoxy)-3,3,5-trimethylcyclohexane, and therefore can be used without scorching or premature cure, according to the disclosure.

U.S. Pat. No. 3,686,102 discloses 2,2-bis(tert-butylperoxy)-4-methylpentane as a bisperoxyketal which can be used at a temperature between that for 1,1-bis(tert-butylperoxy)-3,3,5-trimethylhexane and that for n-butyl-4,4-bis(tert-butylperoxy)valerate. However, this compound has a relatively low molecular weight, and therefore is volatilized in a crosslinking process. Accordingly, only 1,1-bis(tert-butylperoxy)-3,3,5-trimethylcycohexane and n-butyl-4,4-bis(tert-butylperoxy) valerate are sold in the market as crosslinking catalysts.

German Pat. Application No. 2,317,965 laid open to public inspection discloses bis(tert-octylperoxy)alkane. However, this compound is faster in thermal decomposition rate than tert-butyl derivatives, and therefore is not suitable for use as a crosslinking catalyst.

SUMMARY OF THE INVENTION

It is an object of the present invention to provide a crosslinking agent which gives a desirable crosslinking rate to ethylene homopolymers and copolymers.

It is another object of the present invention to provide a crosslinking agent which is easy to handle and gives no odor to crosslinked materials.

It is still another object of the present invention to provide a crosslinking agent which has a low volatility and furnishes the crosslinking process with an excellent operational environment.

The inventors of the present invention reacted cyclododecanone with tert-butylhydroperoxide in an organic solvent using a catalyst such as sulfuric acid, hydrochloric acid, calcium chloride - hydrochloric acid, and cation exchange resin, and thereby synthesized a novel compound having the formula

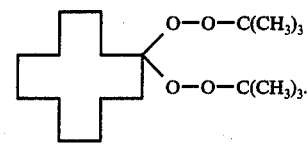

As the organic solvent, aromatic hydrocarbons such as toluene and benzene, and aliphatic hydrocarbons such as n-hexane and cyclohexane are preferably used. The amount of the catalyst is, for instance, when the catalyst is 70 wt.% sulfuric acid, from 140 to 400 g, preferably 200 to 300 g per one mole of cyclododecanone.

The results of the infrared spectrophotometry of this novel compound showed that no absorption of hydroxyl group existed, but an absorption peculiar to peroxides was recognized at 875 cm$^{-1}$. The results of the nuclear magnetic spectrum analysis showed that absorptions of 1.30 PPM (18 H) and 1.45 PPM (22 H) were recognized. The melting point of this novel compound was found to be 67° to 68° C, and the elementary analysis of the novel compound showed that the novel compound contained 69.67 % carbon, 11.86% hydrogen and 18.47% oxygen.

The present invention was made on the basis of the knowledge that this novel compound, 1,1bis(tert-butylperoxy)cyclododecane, has excellent properties as a crosslinking agent as shown in the following:

(1) The crosslinking rate of this novel compound is greater than that of n-butyl 4,4-bis(tert-butylperoxy)valerate and is lower than that of 1,1-bis(tert-butylperoxy)-3,3,5-trimethyl cyclohexane. Therefore, scorching does not occur during the mixing operation (at temperatures of 110° to 130° C) and the crosslinking rate at the cure temperature (140° to 150° C) is rapid.

(2) The odor of the crosslinked composition generated by decomposition of the organic peroxide is weaker than that of n-butyl 4,4-bis(tert-butylperoxy) valerate and is about as strong as that of 1,1-bis(tert-butylperoxy)-3,3,5-trimethylcyclohexane.

(3) Because this novel compound is low in volatility, the loss of the peroxide during the mixing process is small and, consequently, the operational environment is improved.

(4) Because this novel compound has its melting point of 67° to 68° C, it can be mixed with carriers such as calcium carbonate and calcium silicate in any proportion without separation, and therefore it is easily to handle.

(5) The novel compound is a stable peroxide in its pure state, and therefore is easy to handle.

Polymeric materials that can be crosslinked by the crosslinking agent according to the present invention include ethylene homopolymers, ethyl-vinylacetate copolymers, ethylene-propylene rubbers, natural rubber, etc.

The crosslinking agent according to the present invention can be used alone, as a matter of course. In addition, it can be used in the state of an inseparable mixture which are produced by mixing it with carriers such as calcium carbonate and calcium silicte in any proportion, since it is solid at room temperature.

The crosslinking agent according to the present invention may be used in combination with suitable crosslinking coagents such as ethyleneglycoldimethylacrylate and sulfur in a crosslinking process thereby improving the physical properties of the crosslinked materials produced.

Besides, the crosslinking agent according to the present invention may be used together with ordinary fillers such as carbon black, zinc white and manganese dioxide.

The crosslinking process according to the present invention is carried out at pressures of 50 to 200 kg/cm$^2$, at temperatures of 100° to 200° C, preferably at 140° to 170° C, and for 1 to 60 minutes, preferably for 3 to 30 minutes.

The amount of the crosslinking agent to be added is 0.3 to 10 parts by weight, preferably 1 to 5 parts by weight, per 100 parts by weight of polymeric materials.

PREFERRED EMBODIMENTS OF THE INVENTION

EXAMPLE 1

Production of 1,1-bis(tert-butylperoxy)cyclododecane:

Into a four openings flask equipped with a mechanical stirrer, 70 ml of n-hexane, 27.8 g (0.25 mole) of tert-butylhydroperoxide (for industrial use, purity: 81 %, and 18.2 g (0.1 mole) of cyclododecanone were introduced. Then, the solution was cooled to 0° C, and 30g of 70% sulfuric acid were added little by little with stirring. After all the above reactants were added, the reaction mixture was stirred at 0° C for 3 hours. The reaction product mixture was then separated and the organic layer thereof was washed with water until it became neutralized. After the resulting product was dried using anhydrous magnesium sulfate, n-hexane was distilled away therefrom at temperatures of 30° to 40° C under a reduced pressure of 20 mmHg to obtain a white and solid raw product.

In order to remove non-reacted components and impurities the raw product was washed twice with an aqueous solution of 80 % methanol and was then washed with water. It was then dried to obtain 32.1 g of a white and solid refined product. Iodometric titration showed that the purity of the refined product was 98.6 %, and the yield with respect to cyclododecanone was 92 %. Besides, it showed the following properties:

Melting point: 67° – 68° C

| Composition (according to elementary analysis): | | |
|---|---|---|
| | Measured value | Theoretical value |
| C(%) | 69.69 | 69.72 |
| H(%) | 11.86 | 11.70 |

EXAMPLE 2

Properties of 1,1-bis(tert-butylperoxy) cyclododecane and peroxides similar thereto:

In the same manner as in the case of Example 1, cyclododecanone was made to react with each of tert-amylhydroperoxide, 1,1,3,3-tetramethylbutylhydroperoxide and tert-hexylhydroperoxide to synthesize the corresponding bis(tert-alkylperoxy)cyclododecanes.

The thermal decomposition rates of the peroxide according to the present invention, peroxides similar thereto, and publicly known peroxides were measured in benzene. The results are shown in Table 1.

Table 1.

Thermal Decomposition Rate
Solvent: Benzene
Initial concentration: 0.05 mole/1 (0.1 mole/1 for dicumylperoxide)

| Peroxide | Melting point (° C) | Half life(hours) | | |
|---|---|---|---|---|
| | | 90° C | 100° C | 110° C |
| 1,1-bis(tert-butylperoxy)-cyclododecane | 67 – 68 | 20.9 | 5.6 | — |
| 1,1-bis(tert-amylperoxy)-cyclododecane | 15 – 16 | 10.4 | 3.0 | — |
| 1,1-bis(tert-hexylperoxy)-cyclododecane | 35 – 36 | 11.3 | 3.1 | — |
| 1,1-bis(1,1,3,3-tetramethyl-butylperoxy)cyclododecane | | 3.5 | — | — |
| 1,1-bis(tert-butylperoxy)-3,3,5-trimethylcyclohexane | | 10.2 | 3.0 | 0.9 |
| n-butyl 4,4-bis(tert-butylperoxy) valerate | | | 15.9 | 5.6 |
| Dicumylperoxide | | | | 25.6 |

The above results show that the thermal decomposition rate of the peroxide according to the present invention is lowest among those of the similar cyclododecane peroxides, and is lower than that of 1,1-bis(tert-butylperoxy)-3,3,5-trimethylcyclohexane, and is greater than those of n-butyl 4,4-bis(tert-butylperoxy) valerate and dicumylperoxide.

These facts suggest that the peroxide according to the present invention involves no scorching in the mixing process and achieves a high crosslinking rate in the crosslinking process.

Then, tests were conducted on the safety degrees of the peroxide according to the present invention, cyclododecane peroxides similar thereto, and publicly-known peroxides. The results are shown in Table 2.

Table 2.

| Peroxide | Safety Degree | | |
|---|---|---|---|
| | Rapid heat test | Ballistic motar test | Pressure vessel test |
| | Foaming decomp. temp. (° C) | As against TNT (%) | Orifice dia. (mm) |
| 1,1-bis(tert-butylperoxy)-cyclododecane | 119 | 0.63 | 3.5 or less |
| 1,1-bis(tert-amylproxy)-cyclododecane | 115 | 0.61 | 3.5 or less |
| 1,1-bis(tert-hexylperoxy)-cyclododecane | 120 | 0.60 | 3.5 or less |
| 1,1-bis(1,1,3,3-tetramethyl-butylperoxy)cyclododecane | 102 | 0.61 | 3.5 or less |
| 1,1-bis(tert-butylperoxy)-3,3,5-trimethylcyclohexane | 114 | 10.2 | 4.9 |
| n-butyl 4,4-bis(tert-butyl-peroxy) valerate | 129 | 0.81 | 3.5 |
| Dicumylperoxide | 130 | 0.50 | 3.5 or less |

The methods of the above tests conform to "Safety Engineering", Section 4(2), Page 131, written by Kitagawa et al. and published in 1965.

The above results show that the peroxide according to the present invention is stable.

EXAMPLE III

Crosslinking of EPDM:

Crosslinking tests of EPDM (Produced by Sumitomo Chemical Co., Ltd, Trade Name: Esprene) were conducted using the peroxide according to the present invention, cyclododecane peroxides similar thereto, and publicly-known peroxides.

Each peroxide was previously mixed with calcium carbonate, which functioned as a carrier, until the concentration of the peroxide became 40% by weight.

The mixing process was carried out by a roll mixer. Then, the crosslinking process was carried out in a press at a pressure of 150 kg/cm$^2$, at a temperature of 150° C (160° C for dicumylperoxide), and for 10 to 40 minutes.

Table 3 shows the compositions of polymer mixtures, and Table 4 shows the physical properties of the crosslinked materials produced.

Table 3.

| Specimen No. | Compositions of Polymer Mixtures (Parts by Weight) | | | | | | | |
|---|---|---|---|---|---|---|---|---|
| | 1 | 2 | 3 | 4 | 5 | 6 | 7 | 8 |
| EPDM (Esprene 502) | 100 | 100 | 100 | 100 | 100 | 100 | 100 | 100 |
| Stearic acid | 1 | 1 | 1 | 1 | 1 | 1 | 1 | 1 |
| Zinc white | 5 | 5 | 5 | 5 | 5 | 5 | 5 | 5 |
| HAF carbon black | 40 | 40 | 40 | 40 | 40 | 40 | 40 | 40 |
| 1,1-bis(tert-butylperoxy)-cyclododecane | 8.60 | 8.60 | 8.60 | — | — | — | — | — |
| 1,1-bis(tert-amylperoxy)-cyclododecane | — | — | — | 9.30 | — | — | — | — |
| 1,1-bis(tert-hexylperoxy)-cyclododecane | — | — | — | — | 10.0 | — | — | — |
| 1,1-bis(tert-butylperoxy)-3,3,5-trimethylcyclohexane | — | — | — | — | — | 7.55 | — | — |
| n-butyl 4,4-bis(tert-butyl-peroxy) valerate | — | — | — | — | — | 8.35 | — | — |
| Dicumyl peroxide | — | — | — | — | — | — | 6.75 | — |
| Sulphur | — | 0.32 | — | — | — | — | — | — |
| Ethyleneglycol-di-methacrylate | — | — | 3.0 | — | — | — | — | — |

Table 4.

| Specimen No. | | | Physical Properties of Crosslinked Materials | | | | | | | |
|---|---|---|---|---|---|---|---|---|---|---|
| | | | 1 | 2 | 3 | 4 | 5 | 6 | 7 | 8 |
| Curing temperature (° C) | | | 150 | 150 | 150 | 150 | 150 | 150 | 150 | 160 |
| Tensile strength (kg/cm$^2$) | Curing time (min.) | 10 | 200 | 242 | 209 | 130 | 160 | 209 | 180 | 200 |
| | | 20 | 201 | 242 | 203 | 145 | 165 | 202 | 197 | 210 |
| | | 30 | 196 | 244 | 196 | 150 | 170 | 203 | 210 | 220 |
| | | 40 | 198 | 244 | 196 | 155 | 170 | 200 | 210 | 212 |
| Elongation (%) | Curing time (min.) | 10 | 560 | 570 | 330 | 760 | 740 | 540 | 540 | 570 |
| | | 20 | 550 | 580 | 330 | 740 | 740 | 510 | 400 | 450 |
| | | 30 | 560 | 570 | 310 | 740 | 720 | 510 | 400 | 400 |
| | | 40 | 560 | 570 | 310 | 730 | 750 | 510 | 400 | 420 |
| 100% modulus (kg/cm$^2$) | Curing time (min.) | 10 | 16 | 22 | 32 | 14 | 14 | 17 | 17 | 15 |
| | | 20 | 18 | 22 | 32 | 14 | 14 | 16 | 19 | 18 |
| | | 30 | 17 | 21 | 32 | 15 | 14 | 16 | 18 | 19 |
| | | 40 | 18 | 21 | 33 | 15 | 14 | 17 | 19 | 18 |
| 200% modulus (kg/cm$^2$) | Curing time (min.) | 10 | 30 | 44 | 85 | 18 | 21 | 32 | 32 | 31 |
| | | 20 | 31 | 42 | 83 | 19 | 21 | 32 | 34 | 46 |
| | | 30 | 34 | 43 | 84 | 20 | 22 | 34 | 35 | 50 |
| | | 40 | 33 | 41 | 87 | 21 | 21 | 34 | 35 | 48 |
| 300% modulus (kg/cm$^2$) | Curing time (min.) | 10 | 67 | 85 | 181 | 30 | 35 | 67 | 64 | 65 |
| | | 20 | 74 | 83 | 175 | 32 | 37 | 74 | 75 | 105 |
| | | 30 | 72 | 84 | 178 | 33 | 37 | 74 | 76 | 114 |
| | | 40 | 71 | 87 | 181 | 35 | 37 | 73 | 78 | 113 |
| Spring hardness (Hs) | Curing time (min.) | 10 | 61 | 65 | 72 | 57 | 59 | 61 | 61 | 60 |
| | | 20 | 61 | 66 | 71 | 58 | 58 | 61 | 62 | 61 |
| | | 30 | 61 | 66 | 72 | 58 | 58 | 62 | 64 | 62 |
| | | 40 | 62 | 65 | 70 | 59 | 59 | 62 | 62 | 63 |
| Odor | | | None | None | None | None | None | None | Slight | Considerable |
| Blooming | | | None | None | None | None | None | None | None | None |

In Table 4, the term "None" in the column "Blooming" means that there occurred no blooming for three months or more when the crosslinked material in question was kept at room temperature; and the terms "None", "Slight" and "Considerable" in the column "Odor" represent the intensities of odor generated from the crosslinked materials in question when kept at room temperature.

The above results show that the odor generated by decomposition of the organic peroxides in the crosslinked materials when the peroxide according to the present invention, i.e., 1,1-bis(tert-butylperoxy)-cyclododecane, is employed is less than that when the publicly-known peroxides such as dicumyl peroxide and n-butyl 4,4-bis(tert-butylperoxy) valerate are employed, and is as low as that when 1,1-bis(tert-butylperoxy)-3,3,5-trimethylcyclohexane is used; that the physical properties of the crosslinked materials when the peroxide according to the present invention is used are about the same as those in the case where the publicly-known peroxides are employed; and that the peroxide according to the present invention is useful as a crosslinking agent for the above reasons.

In addition, the cyclododecane peroxides similar to the peroxide of the present invention, such as 1,1-bis(tert-amylperoxy)-cyclododecane and 1,1-bis(tert-hexylperoxy)cyclododecane, are low in crosslinking efficiency. Therefore, only the peroxide of the present invention is useful as crosslinking agent among these similar cyclododecane peroxides.

The above results also show that the use of the peroxide of the present invention in combination with crosslinking co-agents such as sulfur and ethyleneglycol-dimethacrylate results in a remarkable improvement in the physical properties of the crosslinked materials produced.

EXAMPLE IV

Comparison of crosslinking rates:

Regarding the peroxide of the present invention, the cyclododecane peroxides similar thereto and the publicly-known peroxides, the crosslinking rates in the crosslinking process of EPDM (Esprene 502) were measured and compared. The crosslinking rates were measured at 150° C using a rheometer. The results are shown in Table 6.

The composition of the polymer mixtures used in this test is as follows:

| EPDM (Esprene 502) | 100 parts by weight |
| Stearic acid | 1 part by weight |
| Zinc white | 5 parts by weight |
| HAF carbon black | 40 parts by weight |
| Peroxide (diluted to 40% with calcium carbonate) | 0.01 mole |

Table 5.

| Comparison of Crosslinking Rates | | |
| --- | --- | --- |
| peroxide | Curing temp. (° C) | Curing time (min.) |
| 1,1-bis(tert-butylperoxy)cyclododecane | 150 | 14 |
| 1,1-bis(tert-amylperoxy)cyclododecane | 150 | 12 |
| 1,1-bis(tert-hexlperoxy)cyclododecane | 150 | 10.5 |
| 1,1-bis(1,1,3,3-tetramethylbutylperoxy)-cyclododecane | 150 | 4.5 |
| 1,1-bis(tert-butylperoxy)-3,3,5-trimethylcyclohexane | 150 | 9.5 |
| n-butyl 4,4-bis)tert-butylperoxy) valerate | 150 | 31 |
| Dicumyl peroxide | 150 | 59 |

EXAMPLE V

Comparision of volatility:

The volatilities of the peroxide of the present invention and the publicy-known peroxides were compared. Tests were carried out using EPDM (Esprene 502) as the polymer.

The mixing process was carried out by a roll mixer. The thus obtained polymer mixtures were allowed to stand laying open in the atmosphere at room temperatures for 10 – 30 days and then were subjected to the crosslinking process in a press at a pressure of 150 kg/cm², at temperature of 150° C and for 20 minutes. The physical properties of the resultant crosslinked materials were measured and the results are shown in Table 6.

In Table 6, the term "yes" or "none" in the column Existence of volatility" was determined depending on whether the physical properties of the crosslinked material were deteriorated or not, because when the peroxide in a polymer is volatilized, the percentage of the peroxide in the polymer mixture is decreased, with the result being that the physical properties of the crosslinked material is as a matter of course deteriorated.

The composition of the polymer mixtures used in this test is as follows:

| EPDM (Esprene 502) | 100 parts by weight |
| Stearic acid | 1 part by weight |
| Zinc white | 5 parts by weight |
| HAF carbon black | 40 parts by weight |
| Peroxide (diluted to 40% with calcium carbonate) | 0.01 mole |

The tensile strength and elongation of the crosslinked material was measured according to the same method as that described in Example 3.

The above results show that the physical properties of a crosslinked material obtained from a polymer mixture containing the peroxide of the present invention which was laid open in the atmosphere for 30 days, was not deteriorated, and that the peroxide of the present invention volatizes a very little (or scarcely any) and is good because the loss of the peroxide due to volatilization is very little during the mixing process.

Table 6.

| | | Comparision of Volatility | | | | | | |
| --- | --- | --- | --- | --- | --- | --- | --- | --- |
| | | Physical Properties | | | | | | |
| Peroxide | Days laid open | Tensile strength (kg/cm²) | Elongation % | 100 % modulus (kg/cm²) | 200% modulus (kg/cm²) | 300 % modulus (kg/cm²) | spring hardness (HS) | existence of volatility |
| 1,1-bis(tert-butylperoxy) cyclododecane | 0 | 201 | 550 | 18 | 31 | 74 | 61 | None |
| | 10 | 200 | 550 | 18 | 30 | 75 | 61 | |
| | 20 | 202 | 540 | 17 | 32 | 74 | 61 | |
| | 30 | 201 | 550 | 18 | 31 | 74 | 62 | |
| 1,1-bis(tert-butylperoxy)-3,3,5-trimethyl-cyclohexane | 0 | 202 | 510 | 16 | 32 | 74 | 61 | consider-able |
| | 10 | 190 | 510 | 15 | 31 | 72 | 61 | |
| | 20 | 188 | 500 | 14 | 29 | 68 | 60 | |
| | 30 | 160 | 510 | 14 | 27 | 60 | 68 | |
| n-butyl 4,4-bis(tert-butylperoxy) valerate | 0 | 197 | 400 | 19 | 34 | 75 | 62 | slightly yes |
| | 10 | 195 | 400 | 19 | 35 | 74 | 62 | |
| | 20 | 195 | 410 | 19 | 34 | 74 | 61 | |
| | 30 | 180 | 400 | 18 | 33 | 70 | 61 | |

EXAMPLE VI

Crosslinking velocity at 120° C (Comparison of existence of scorching)

Regarding the peroxide of the cyclododecane present invention, the peroxides similar thereto and the publicly-known peroxides, the crosslinking velocity at 120° C (mixing temperature) in the crosslinking process of EPDM (Esprene 502) was measured by a rheometer, to thereby compare the existence of the scorching of respective crosslinking materials. The attached drawing shows the rheometer curves for several kinds of peroxides. Curve (1) is for 1,1-bis(t-butylperoxy)3,3,5-trimethylcyclohexane, curve (2) for 1,1-bis(t-butylperoxy)cyclododecane, curve (3) for n-butyl 4,4-bis(t-butylperoxy) valerate and curve (4) is for dicumylperoxide.

Existence of scorching was determined by the result of whether or not the time consumed for increasing the torque value in the respective rheometer curves by an amount of 5 Kg. cm the from the minimum value is less than 30 minutes. Namely, there is danger of scorching accurring when the time is less than 30 minutes, but when the time is more than 30 minutes, scorching does not take place. The composition of the polymer mixtures used in this test is same as that used in the preceding Examples. The above results and the results of Example 2 show that the peroxide of the present invention is faster in crosslinking velocity than dicumylperoxide and n-butyl 4,4-bis(tert-butylperoxy) valerate and is slower than 1,1-bis (tert-butylperoxy)3,3,5- trimethylcyclohexane and accordingly, according to the present invention, scorching does not occur at the mixing temperature (110°–130° C) but the crosslinking velocity is fast at the crosslinking temperature (140–150° C).

Table 7.

Crosslinking velocity at 120° C
(Comparision of existence of scorching)

| Peroxide | Time consumed for increasing torque value 5 kgcm from the minimum value thereof (min) | Danger of Scorching |
|---|---|---|
| 1,1-bis(tert-butylperoxy)cyclododecane | 45 | none |
| 1,1-bis(tert-butylperoxy)3,3,5-trimethyloyclohexane | 20 | yes |
| n-butyl 4,4-bis(tert-butylperoxy)valerate | 55 | none |
| Dicumyl peroxide | 90 up | none |

EXAMPLE VII

Crosslinking tests of ethylene-vinyl acetate copolymer (produced by Japan Polychemical Co., Ltd., Trade Name: Ultrasen 637) using the peroxide of the present invention, cyclododecane peroxides similar thereto and publicy-known peroxides.

The mixing process of the polymer mixtures, crosslinking reaction, tension tests, evaluation of odor and blooming were conducted in the same manner as that described in Examiner 1.

The compositions of the polymer mixtures, and the physical properties of crosslinked materials are shown respectively in Table 8 and Table 9.

Table 8.

| Specimen No. | Composition of Polymer Mixture (Parts by weight) | | | | | |
|---|---|---|---|---|---|---|
|  | 1 | 2 | 3 | 4 | 5 | 6 |
| Ethylene-vinyl acetate-copolymer (ultrasen 634) | 100 | 100 | 100 | 100 | 100 | 100 |
| Stearic acid | 1 | 1 | 1 | 1 | 1 | 1 |
| 1,1-bis(tert-butylperoxy)-cyclododecane | 8.60 | — | — | — | — | — |
| 1,1-bis(tert-amylperoxy)-cyclododecane | — | 9.30 | — | — | — | — |
| 1,1-bis(tert-hexylperoxy)-cyclododecane | — | — | 10.0 | — | — | — |

Table 8.-continued

| Specimen No. | Composition of Polymer Mixture (Parts by weight) | | | | | |
|---|---|---|---|---|---|---|
|  | 1 | 2 | 3 | 4 | 5 | 6 |
| 1,1-bis(tert-butylperoxy)3,3,5-trimethylcyclohexane | — | — | — | 7.55 | — | — |
| n-butyl 4,4-bis(tert-butyl-peroxy)valerate | — | — | — | — | 8.35 | — |
| Dicumyl peroxide | — | — | — | — | — | 6.75 |

Table 9.

| Specimen No. | | | Physical Properties of Crosslinked Material | | | | | |
|---|---|---|---|---|---|---|---|---|
|  |  |  | 1 | 2 | 3 | 4 | 5 | 6 |
| Curing temperature (° C) |  |  | 150 | 150 | 150 | 150 | 150 | 160 |
| Tensile strength (Kg/cm$^2$) | Curing time (min.) | 10 | 301 | 255 | 240 | 302 | 277 | 297 |
|  |  | 20 | 310 | 250 | 245 | 318 | 249 | 289 |
|  |  | 30 | 310 | 230 | 230 | 298 | 241 | 263 |
|  |  | 40 | 295 | 210 | 230 | — | — | — |
| Elongation (%) | Curing time (min.) | 10 | 570 | 570 | 550 | 550 | 590 | 520 |
|  |  | 20 | 540 | 580 | 560 | 560 | 560 | 490 |
|  |  | 30 | 550 | 570 | 560 | 570 | 550 | 490 |
|  |  | 40 | 560 | 560 | 550 | — | — | — |
| 100% modulus (Kg/cm$^2$) | Curing time (min.) | 10 | 36 | 35 | 33 | 35 | 34 | 35 |
|  |  | 20 | 36 | 34 | 33 | 35 | 34 | 34 |
|  |  | 30 | 35 | 30 | 33 | 34 | 33 | 33 |
|  |  | 40 | 34 | 30 | 34 | — | — | — |
| 200% modulus (Kg/cm$^2$) | Curing time (min.) | 10 | 43 | 41 | 41 | 43 | 40 | 42 |
|  |  | 20 | 46 | 38 | 41 | 11 42 | 41 | 41 |
|  |  | 30 | 43 | 38 | 41 | 41 | 40 | 41 |
|  |  | 40 | 40 | 38 | 40 | — | — | — |
| 300% modulus (Kg/cm$^2$) | Curing time (min.) | 10 | 53 | 48 | 51 | 55 | 50 | 52 |
|  |  | 20 | 57 | 46 | 50 | 52 | 50 | 52 |
|  |  | 30 | 54 | 45 | 50 | 52 | 50 | 51 |
|  |  | 40 | 50 | 47 | 51 | — | — | — |
| Odor |  |  | none | none | none | none | slight | considerable |
| Blooming |  |  | none | none | none | none | none | none |

The above results show that the odor of the crosslinked composition generated by decomposition of the peroxide of the present invention as well as in case of crosslinking EPDM as shown in Example 3, is less than that generated by decomposition of publicly known peroxides, for instance, dicumylperoxide or n-butyl 4,4-bis(tert-butylperoxy) valerate and is same as that of 1,1-bis(tert-butylperoxy) 3,3,5-trimethylcyclohexane and the physical properties of the crosslinked composition are the same as those obtained by the publicly-known peroxides and the peroxide of the present invention is very useful as a crosslinking agent. The above results show that 1,1-bis(t-amylperoxy)cyclododecane and 1,1-bis(t-hexylperoxy)cyclododecane, which are cyclododencane peroxides similar to that of the present invention are low in the efficiency of crosslinking and also the surface of the crosslinking composition is not uniform and accordingly said peroxides are not preferable as crosslinking agents.

Extraction tests with chloroform:

Tests of extracting ethylene-vinyl acetate copolymer which was crosslinked by the peroxide of the present invention, and peroxide similar thereto, with chloroform, were carried out. A crosslinked composition of about 1mm square was weighed accurately on a brass net of 100 mm mesh and the net was folded into a bag so that the crosslinked composition did not escape.

Then the crosslinked composition was extracted with chloroform for 8 hours using a Soxhlet extractor.

The chloroform was renewed every 6–8 hours. After extraction, the net and its contents were put into a vacuum decicator and were dried at 50° C to get a constant weight thereof. The resultant gel was weighed and the percentage of its weight based on the weight of the starting material, was calculated.

When the percentage of the resultant gel is over 90%, the crosslinking reaction was conducted completely.

The results are shown in Table 10. The specimens used in these tests were the same as those used in the preceding Examples for measuring the physical properties therefor.

Table 10.

| Curing time (min.) | Extraction tests with chloroform resultant quantity of gel (%) | | | | | |
|---|---|---|---|---|---|---|
| | Specimen No. | | | | | |
| | 1 | 2 | 3 | 4 | 5 | 6 |
| 10 | 92.7 | 88.7 | 88.3 | 92.2 | 92.0 | 95.5 |
| 20 | 92.4 | 87.9 | 87.7 | 92.6 | 92.6 | 97.0 |
| 30 | 92.6 | 88.3 | 88.7 | 92.1 | 92.7 | 96.5 |
| 40 | 92.3 | 89.8 | 88.4 | 92.2 | 92.6 | 96.7 |

The above results show that the peroxide of the present invention produces as much gels as the publicly known peroxides do and the crosslinking reaction with the peroxide of the present invention is completely conducted, whereas the percentage of gel product for 1,1-bis(tert-amylperoxy)cyclododecane and 1,1-bis(tert-hexylperoxy)cyclododecane is less than 90% and neither crosslinking reaction was sufficiently conducted.

What is claimed is:

1. A process for crosslinking a polymeric material which comprises treating said polymeric material with a crosslinking agent composition comprising 1,1-bis (tert-butylperoxy)cyclododecane at a pressure of 50 to 200 kg/cm² and at a temperature of 100° to 200° C.

2. The process for crosslinking a polymeric material as set forth in claim 1, wherein 1 to 5 parts by weight of 1,1-bis(tert-butylperoxy)cyclododecane is added for 100 parts by weight of said polymeric material.

3. The process for crosslinking a polymeric material as set forth in claim 1, wherein said polymeric material is selected from the group consisting of ethylene homopolymer, ethylene-vinylacetate copolymer, olefin copolymer, ethylene-propylene rubber and natural rubber.

4. A process for crosslinking a polymeric material as set forth in claim 10 in which the crosslinking agent composition contains at least one of calcium carbonate and calcium silicate mixed therein.

5. A process for crosslinking a polymeric material as set forth in claim 10 in which the crosslinking agent composition contains at least one of ethyleneglycoldimethacrylate and sulfur mixed therein.

6. The process for crosslinking a polymeric material as set forth in claim 10, in which the crosslinking agent composition contains at least one of carbon black, zinc white and manganese dioxide mixed therein.

7. A process for crosslinking in which the crosslinking agent composition contains a polymeric material as set forth in claim 4, at least one of ethyleneglycoldimethacryate and sulfur mixed therein.

8. A process for crosslinking in which the crosslinking agent composition contains a polymeric material as set forth in claim 4, at least one of carbon black, zinc white and manganese dioxide mixed therein.

9. A process for crosslinking in which the crosslinking agent composition contains a polymeric material as set forth in claim 7, at least one of carbon black, zinc white and manganese dioxide mixed therein.

* * * * *

UNITED STATES PATENT AND TRADEMARK OFFICE
CERTIFICATE OF CORRECTION

PATENT NO. : 4 093 786
DATED : June 6, 1978
INVENTOR(S) : Takeshi Komai et al

It is certified that error appears in the above-identified patent and that said Letters Patent are hereby corrected as shown below:

Column 12, line 16; change "The" to ---A---.

line 20; after "crosslinking" insert ---a polymeric material as set forth in Claim 4,---.

line 21; delete "a polymeric material as".

line 22; delete "set forth in Claim 4,".

line 24; after "crosslinking" insert ---a polymeric material as set forth in Claim 4,---.

line 25; delete "a polymeric material as".

line 26; delete "set forth in Claim 4,".

line 28; after "crosslinking" insert ---a polymeric material as set forth in Claim 7,---.

UNITED STATES PATENT AND TRADEMARK OFFICE
CERTIFICATE OF CORRECTION

PATENT NO. : 4 093 786
DATED : June 6, 1978
INVENTOR(S) : Takeshi Komai et al

It is certified that error appears in the above-identified patent and that said Letters Patent are hereby corrected as shown below:

Column 12, line 29; delete "a polymeric material as".

line 30; delete "set forth in Claim 7,".

Signed and Sealed this

Fourteenth Day of November 1978

[SEAL]

Attest:

RUTH C. MASON
Attesting Officer

DONALD W. BANNER
Commissioner of Patents and Trademarks